United States Patent [19]

Yokoyama et al.

[11] Patent Number: 4,534,978

[45] Date of Patent: Aug. 13, 1985

[54] PERFLUOROCYCLOAMINES

[75] Inventors: Kazumasa Yokoyama, Toyonaka; Chikara Fukaya, Osaka; Yoshio Tsuda, Takarazuka; Taizo Ono, Osaka; Yoshio Arakawa, Suita; Tadakazu Suyama, Kyoto, all of Japan

[73] Assignee: The Green Cross Corporation, Osaka, Japan

[21] Appl. No.: 633,085

[22] Filed: Jul. 24, 1984

Related U.S. Application Data

[62] Division of Ser. No. 454,107, Dec. 28, 1982, abandoned.

[51] Int. Cl.³ .............................................. C07D 265/32
[52] U.S. Cl. ..................... 514/429; 514/317; 514/212
[58] Field of Search .................. 424/244, 267, 274

[56] References Cited

U.S. PATENT DOCUMENTS

| | | | |
|---|---|---|---|
| 3,235,561 | 2/1966 | Haszeldine et al. | 548/400 |
| 3,911,138 | 4/1975 | Clark, Jr. | 424/352 |
| 3,933,831 | 1/1976 | De Pasquale et al. | 546/192 |
| 3,956,293 | 5/1976 | Pavlik | 548/400 |
| 3,962,439 | 1/1976 | Yokoyama et al. | 424/248 |

FOREIGN PATENT DOCUMENTS 1668794  1/1973  Fed. Rep. of Germany ...... 548/400

OTHER PUBLICATIONS

J. Chem. Soc., Perkin Trans I; No. 8, pp. 781–784 (1975).

Primary Examiner—Maurice J. Welsh
Attorney, Agent, or Firm—Cushman, Darby & Cushman

[57] ABSTRACT

Perfluorocycloamines represented by the general formula:

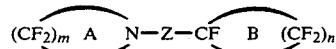

wherein either or both of ring A and ring B may be substituted with lower perfluoroalkyl group(s), m and n are independently 4, 5, or 6 and Z is a perfluoroalkylene group or a mere bond.

3 Claims, No Drawings

PERFLUOROCYCLOAMINES

This is a division of application Ser. No. 454,107, filed Dec. 28, 1982, and now abandoned.

This invention relates to novel perfluorocycloamines useful as oxygen-carrying components for blood substitute, oxygen-carrying transfusions and the like.

More specifically, this invention relates to perfluorocycloamines represented by the general formula:

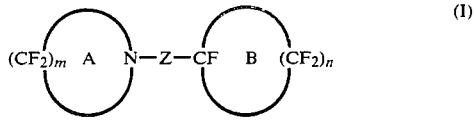

wherein either or both of ring A and ring B may be substituted with lower perfluoroalkyl group(s), m and n are independently 4, 5, or 6 and Z is a perfluoroalkylene group or a mere bond.

In the general formula (I), either or both of ring A and ring B may be substituted with lower perfluoroalkyl group(s) at one or more optional positions (preferably 1 to 2 positions).

Such perfluoroalkyl groups as substituent are linear or branched. Examples of these groups are perfluoromethyl group, perfluoroethyl group, perfluoro-n-propyl group, perfluoro-iso-propyl group, etc., each having 1 to 3 and preferably 1 to 2 carbon atoms. When these substituents are present in the number of 2 or more, they may be different from each other.

With respect to Z in the general formula (I), the perfluoroalkylene group is linear or branched. Examples are, for instance, linear perfluoroalkylene groups of 1 to 3 carbon atoms such as perfluoromethylene, perfluoroethylene and the like and branched perfluoroalkylene groups which are the above perfluoroalkylene groups having a substituent of a lower perfluoroalkyl group of 1 to 2 carbon atoms such as perfluoromethyl or perfluoroethyl. The total carbon atom number of Z, when Z is a perfluoroalkylene group, is usually 1 to 3 and preferably 1 to 2.

The total carbon atom number of the compound of the general formula (I) is usually 8 to 12, preferably 9 to 11, and more preferably 10.

The compound of the general formula (I) can be produced by fluorinating a perhydrocompound corresponding to the compound (I). As the fluorination method, there may be mentioned, for example, known fluorination methods such as the direct fluorination method, the cobalt fluorination method, the electrolytic fluorination method, etc.

In the production of the compound (I) of this invention, the use of the electrolytic fluorination method is preferable. The method can be carried out, for example, by adding into an electrolytic cell anhydrous hydrofluoric acid and a perhydrocompound as starting material compound, making them a solution by mixing and thereafter subjecting the solution to electrolysis. Normally, the voltage used in the electrolysis is 3 to 9 V, the anode current density is 1 to 300 A/dm$^2$ and the cell temperature is 4° to 10° C.

The compound of the general formula of (I) thus formed, is insoluble in anhydrous hydrogen fluoride, so that it precipitates at the bottom layer of the electrolytic cell.

The isolation and refining of the compound (I) from the precipitate is carried out, for example, by adding to the recovered precipitate a mixture of an equal volume of an aqueous alkali solution and an amine compound, subjecting the whole mixture to refluxing, then separating the compound (I) of the lowermost layer (at this time, partially fluorinated compounds are dissolved in the amine layer), washing the compound (I) with an appropriate amount of an aqueous acetone solution containing potassium iodide to remove compounds having nitrogen atoms combining with fluorine atoms, and thereafter conducting a fractional distillation to collect the compound (I).

The compound (I) according to this invention can dissolve a large volume of oxygen and, moreover, is inactive from the standpoint of metabolism and is rapidly excreted out of the human body. Accordingly, for example, an aqueous emulsion containing 5 to 50% (w/v) and preferably 10 to 40% (w/v) of the compound (I) can be used as an oxygen-carrying compound in blood substitute, oxygen-carrying transfusions, etc. which are applied to mammals such as humans, dog, cat, cattle, horse, rat, mouse, guinea pig, etc.

In the preparation of the above emulsion, there are used emulsifiers such as high molecular, non-ionic surfactants, phospholipids, etc., in quantities of 1 to 5% (w/v) each alone or in combination.

In the preparation of the above emulsion, there is also used, as a medium, a physiologically acceptable aqueous solution. If necessary, there may be further added an isotonizing amount of an isotonizing agent such as glycerol to isotonize the emulsion and a plasma extender such as hydroxyethylstarch or dextran to adjust the colloid osmotic pressure of the emulsion.

By homogenizing the above-mentioned ingredients into particles having sizes of 0.05 to 0.3$\mu$, preferably 0.2$\mu$ or smaller using a high-pressure jet-type homogenizer, an aqueous emulsion containing the compound (I) can be prepared.

Incidentally, the perhydrocompounds as starting material corresponding to the compound (I) is substantially known compounds.

This invention will be illustrated in more detail below by the way of Examples and Reference Examples, however, the invention is not restricted by these Examples.

EXAMPLE 1

There was used the following electrolytic cell:
Made of a Monel metal.
Capacity: 1.5 liters
Electrode plates: 6 anode plates and 7 cathode plates, each made of nickel of a purity of at least 99.6%. Anode and cathode plates are alternately arranged with an electrode to electrode distance of 1.7 to 2.0 mm. Effective anode area is 10.5 dm$^2$.
Reflux condenser: Made of copper and placed at the top of cell.

Into this electrolytic cell there was introduced 1.2 liters of anhydrous hydrofluoric acid, and trace amounts of impurities (water and sulfuric acid) were removed by pre-electrolysis. Then, 0.85 mole (130 g) of N-cyclohexylpyrrolidine was dissolved in the hydrofluoric acid and, while helium gas was passed through the cell from the bottom at a rate of 100 ml/min, an electrolysis of 920 Ahr was conducted with an anode current density of 0.4 to 2.0 A/dm$^2$ and an electrolytic voltage of 5 to 9 V at a cell temperature of 4° to 10° C. Hydrofluoric acid was supplemented by each 350 ml per 24 hr. The condensation and subsequent collection of the volatile decomposition products formed during the electrolysis was not conducted. After the electrolysis, the liquid inside the cell separated into two layers, with the upper layer being anhydrous hydrofluoric acid and the lower layer being fluorocarbons. The lower layer was collected from the drain of the cell and 303 g was obtained (yield: 72%). To the collected lower layer which was a fluorinated product by electrolysis, were added 70% aqueous KOH solution and diisobutylamine in equal volumes, and the whole mixture was subjected to refluxing for about 7 days. The reaction mixture was cooled in an ice bath, whereby the perfluorocompound settled as the lowermost layer. The perfluorocompound was then separated using a separation funnel and subsequently washed with water, concentrated sulfuric acid, an aqueous sodium bicarbonate solution, an aqueous acetone solution containing potassium iodide and water in this order to obtain 92 g of a transparent perfluorocompound. The perfluorocompound thus obtained was subjected to fractional distillation in a fractional distillation apparatus with a spinning band column to obtain 32.2 g (yield: 7.7%) of perfluoro-N-cyclohexylpyrrolidine having a boiling point of 145° to 152° C. This compound was verified to be the above-mentioned objective compound also from analysis by IR spectrum, F NMR spectrum, mass spectrum, etc.

EXAMPLES 2 TO 58

In the same manner as in Example 1, corresponding perfluorocompounds were produced from perhydrocompound materials. Materials used and products obtained were summarized in Table 1.

| Example No. | Raw material compound | Perfluorocompound | Boiling point (°C./760 mm Hg) |
|---|---|---|---|
| 2 | N—cyclopentylpyrrolidine | (perfluoro-N-cyclopentylpyrrolidine structure) | 125–135 |
| 3 | N—cyclopentyl-2-methylpyrrolidine | (structure with CF$_3$) | 144–153 |
| 4 | N—cyclopentyl-3-methylpyrrolidine | (structure with CF$_3$) | 144–154 |
| 5 | N—2-methylcyclopentylpyrrolidine | (structure with CF$_3$) | 144–154 |
| 6 | N—8-methylcyclopentylpyrrolidine | (structure with CF$_3$) | 144–154 |
| 7 | N—1-methylcyclopentylpyrrolidine | (structure with CF$_3$) | 144–154 |
| 8 | N—cyclopentylpiperidine | (perfluoro-N-cyclopentylpiperidine structure) | 145–152 |
| 9 | N—cyclopentyl-2-ethylpyrrolidine | (structure with CF$_2$CF$_3$) | 155–165 |

-continued

| Example No. | Raw material compound | Perfluorocompound | Boiling point (°C./760 mm Hg) |
|---|---|---|---|
| 10 | N—cyclopentyl-3-ethylpyrrolidine | (structure with CF$_2$CF$_3$) | 155–164 |
| 11 | N—2-ethylcyclopentylpyrrolidine | (structure with CF$_2$CF$_3$) | 155–163 |
| 12 | N—8-ethylcyclopentylpyrrolidine | (structure with CF$_2$CF$_3$) | 156–165 |
| 13 | N—1-ethylcyclopentylpyrrolidine | (structure with CF$_2$CF$_3$) | 155–164 |
| 14 | N—cyclopentyl-2,3-dimethyl-pyrrolidine | (structure with CF$_3$, CF$_3$) | 154–164 |
| 15 | N—cyclopentyl-2,4-dimethyl-pyrrolidine | (structure with CF$_3$, CF$_3$) | 155–164 |
| 16 | N—cyclopentyl-2,5-dimethyl pyrrolidine | (structure with CF$_3$, CF$_3$) | 154–164 |
| 17 | N—1-methylcyclopentyl-2-methylpyrrolidine | (structure with CF$_3$, CF$_3$) | 155–164 |
| 18 | N—2-methylcyclopentyl-2-methyl-pyrrolidine | (structure with CF$_3$, CF$_3$) | 155–165 |
| 19 | N—3-methylcyclopentyl-2-methyl-pyrrolidine | (structure with CF$_3$, CF$_3$) | 154–153 |

-continued

| Example No. | Raw material compound | Perfluorocompound | Boiling point (°C./760 mm Hg) |
|---|---|---|---|
| 20 | N—cyclopentyl-3,4-dimethyl-pyrrolidine | 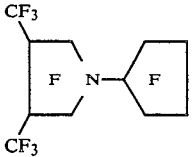 | 155–165 |
| 21 | N—1-methylcyclopentyl-8-pyrrolidine | 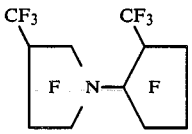 | 154–164 |
| 22 | N—2-methylcyclopentyl-3-methylpyrrolidine | 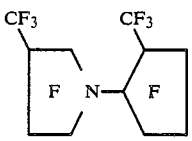 | 155–164 |
| 23 | N—3-methylcyclopentyl-3-methyl-pyrrolidine | 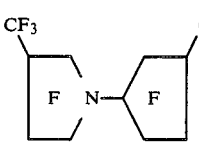 | 155–164 |
| 24 | N—1,2-dimethylcyclopentyl-pyrrolidine | 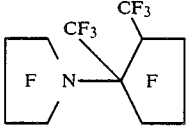 | 155–165 |
| 25 | N—1,3-dimethylcyclopentyl-pyrrolidine | 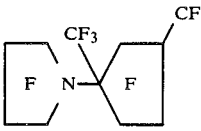 | 155–164 |
| 26 | N—2,3-dimethylcyclopentyl-pyrrolidine | 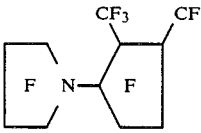 | 155–164 |
| 27 | N—2,4-dimethylcyclopentyl-pyrrolidine | 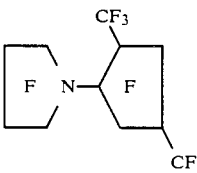 | 155–164 |
| 28 | N—2,5-dimethylcyclopentyl-pyrrolidine | 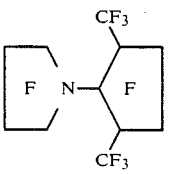 | 154–168 |
| 29 | N—8,4-dimethylcyclopentyl-pyrrolidine | 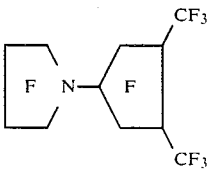 | 155–164 |

-continued

| Example No. | Raw material compound | Perfluorocompound | Boiling point (°C./760 mm Hg) |
|---|---|---|---|
| 30 | n-cyclopentyl-2,2-dimethyl-pyrrolidine | 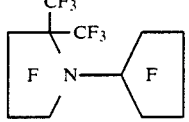 | 154–163 |
| 31 | N—cyclopentyl-3,3-dimethyl-pyrrolidine | 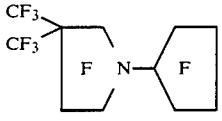 | 154–163 |
| 32 | N—2,2-dimethylcyclopentyl-pyrrolidine | 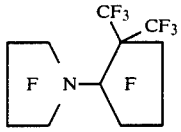 | 155–165 |
| 33 | N—3,3-dimethylcyclopentyl-pyrrolidine | 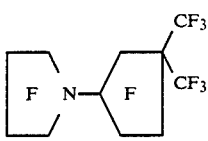 | 155–165 |
| 34 | N—cyclohexyl-2-methyl-pyrrolidine | 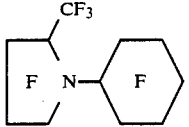 | 155–165 |
| 35 | N—cyclohexyl-3-methyl-pyrrolidine | 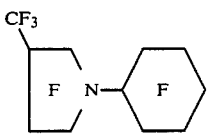 | 154–165 |
| 36 | N—1-methylcyclohexyl-pyrrolidine | 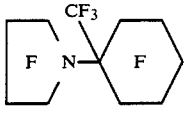 | 155–165 |
| 37 | N—2-methylcyclohexyl-pyrrolidine | 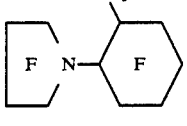 | 156–165 |
| 38 | N—3-methylcyclohexyl-pyrrolidine | 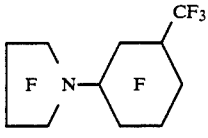 | 156–165 |
| 39 | N—4-methylcyclohexyl-pyrrolidine | 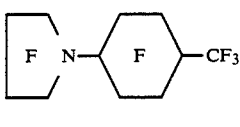 | 155–165 |
| 40 | N—cyclopentyl-2-methyl-piperidine | 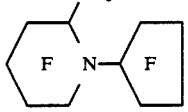 | 156–165 |

-continued

| Example No. | Raw material compound | Perfluorocompound | Boiling point (°C./760 mm Hg) |
|---|---|---|---|
| 41 | N—cyclopentyl-3-methyl-piperidine | 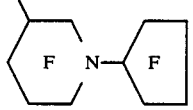 | 156-165 |
| 42 | N—cyclopentyl-4-methyl-piperidine | 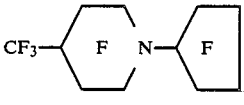 | 156-165 |
| 43 | N—1-methylcyclopentyl-piperidine | 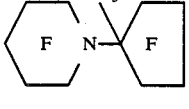 | 156-165 |
| 44 | N—2-methylcyclopentyl-piperidine | 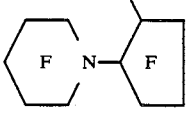 | 155-165 |
| 45 | N—3-methylcyclopentyl-piperidine | 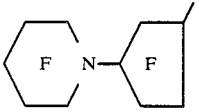 | 156-155 |
| 46 | N—cyclopentylmethyl-pyrrolidine | 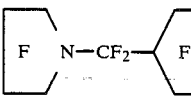 | 145-155 |
| 47 | N—cyclopentylmethyl-2-methyl pyrrolidine | 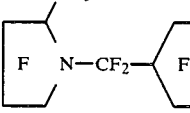 | 156-165 |
| 48 | N—cyclopentylmethyl-3-methyl-pyrrolidine | 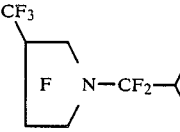 | 156-165 |
| 49 | N—(1-cyclopentyl)ethyl-pyrrolidine | 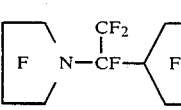 | 156-165 |
| 50 | N—(1-methylclopentyl)methyl-pyrrolidine | 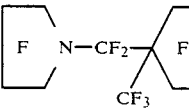 | 156-165 |
| 51 | N—(2-methylcyclopentyl)methyl-pyrrolidine | 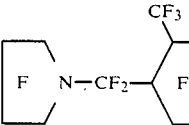 | 156-165 |

-continued

| Example No. | Raw material compound | Perfluorocompound | Boiling point (°C./760 mm Hg) |
|---|---|---|---|
| 52 | N—(3-methylcyclopentyl)methyl pyrrolidine | 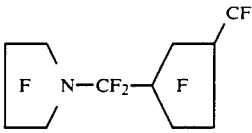 | 156–165 |
| 53 | N—cyclohexylmethylpyrrolidine | 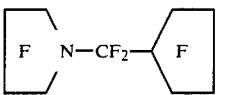 | 156–165 |
| 54 | N—cyclopentylmethyl-piperidine | 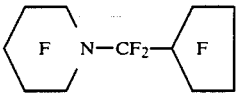 | 156–165 |
| 55 | N—cyclopentylhexahydroazepine | 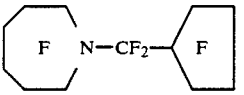 | 156–165 |
| 56 | N—cycloheptylpyrrolidine | 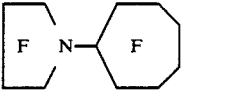 | 155–165 |
| 57 | N—(2-cyclopentyl)ethyl-pyrrolidine | 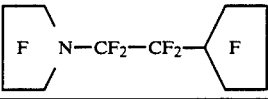 | 155–165 |

REFERENCE EXAMPLE 1

400 g of vitelline phospholipid was added to 8.5 l of lactic acid added Ringer's solution, and stirred by a mixer to prepare a coarse emulsion, then 2.5 kg of perfluoro-N-cyclohexylpyrrolidine was added thereto and stirred vigorously again by the mixer to prepare a coarse emulsion. This coarse emulsion was placed in a liquid tank of a jet emulsifier (manufactured by Manton-Gaulin Co.) and circulated while maintaining the liquid temperature at 50°±5° C. to effect emulsification. The concentration of perfluoro-N-cyclohexylpyrrolidine in the obtained emulsion was 27.3% (w/v). The particle diameter as measured by the centrifugal sedimentation method was 0.05–0.25μ. This emulsion was allotted into vials for injection, stoppered and thermally sterilized in a rotary sterilizer, but there was no significant increase in the particle diameter observed.

REFERENCE EXAMPLE 2

An emulsion was obtained by procedures similar to those in Reference Example 1 except that perfluoro-N-cyclohexylprrolidine was replaced by perfluoro-N-(3'-methylcyclohexyl)pyrrolidine. The particle diameter of the thus obtained emulsion was 0.05–0.25μ.

EXPERIMENTAL EXAMPLE 1

Stability of Emulsions

Water was added to 20 g of each perfluorocycloamine selected in the present invention and 4 g of vitelline phospholipid to make the total volume 200 ml, and emulsification was effected using a Manton-Gaulin emulsifier as used above under nitrogen stream at 200–600 kg/cm² while maintaining the liquid temperature at 40°–45° C. Each obtained emulsion was filtered through a 0.65μ membrane filter, allotted into 20 ml capacity vials, and, after replacing the atmosphere by nitrogen gas, thermally treated at 100° C. for 30 minutes, followed by storing at 4° C. of room temperature to examine the stability. The particle diameter of the emulsion was measured by the centrifugal sedimentation method by Yokoyama et al. [Chem. Pharm. Bull. 22 (12) 2966 (1974)], and from the obtained data, the average particle diameter distribution was calculated using a microcomputer.

Thus, the particle diameter distributions of each perfluorocarbon emulsion before and after heating, and after heating and storing at 4° C. and room temperature (15°–28° C.) are shown in Tables 2 and 3. As is evident from the results, the emulsions according to the present invention are very stable against heating and the influence on the average particle diameter due to heating was not observed at all. Further, when stored at 4° C. after heating, there was no increase in the average particle diameter of the emulsion observed even after 5 months.

TABLE 2

Stability of Perfluoro-N—cyclohexylpyrrolidine Emulsion

| | Average Particle Diameter, μ | Distribution of Particle Diameter (wt %) | | | |
|---|---|---|---|---|---|
| | | <0.1μ | 0.1–0.2μ | 0.2–0.3μ | >0.3μ |
| Before heating | 0.114 | 40.1 | 52.7 | 7.2 | 0 |
| Immediately after heating | 0.115 | 39.1 | 56.9 | 4.0 | 0 |
| After 2 weeks | | | | | |

TABLE 2-continued

Stability of Perfluoro-N—cyclohexylpyrrolidine Emulsion

| | Average Particle Diameter, μ | Distribution of Particle Diameter (wt %) | | | |
|---|---|---|---|---|---|
| | | <0.1μ | 0.1–0.2μ | 0.2–0.3μ | >0.3μ |
| at 4° C. | 0.114 | 40.3 | 58.4 | 1.3 | 0 |
| at R.T.* | 0.122 | 39.6 | 58.6 | 1.8 | 0 |
| After 4 weeks | | | | | |
| at 4° C. | 0.113 | 39.0 | 58.1 | 2.9 | 0 |
| at R.T.* | 0.122 | 33.1 | 60.9 | 6.0 | 0 |
| After 5 months at 4° C. | 0.114 | 40.3 | 57.4 | 2.3 | 0 |

*R.T. = Room Temperature

TABLE 3

Stability of Perfluoro-N—(3'-methylcyclohexyl)-pyrrolidine Emulsion

| | Average Particle Diameter, μ | Distribution of Particle Diameter (wt %) | | | |
|---|---|---|---|---|---|
| | | <0.1μ | 0.1–0.2μ | 0.2–0.3μ | >0.3μ |
| Before heating | 0.133 | 28.0 | 62.7 | 9.3 | 0 |
| Immediately after heating | 0.132 | 28.5 | 63.4 | 8.1 | 0 |
| After 2 weeks | | | | | |
| at 4° C. | 0.131 | 28.1 | 64.2 | 7.7 | 0 |
| at R.T.* | 0.133 | 27.5 | 65.3 | 7.2 | 0 |
| After 4 weeks | | | | | |
| at 4° C. | 0.132 | 27.8 | 64.3 | 7.9 | 0 |
| at R.T.* | 0.135 | 26.8 | 66.3 | 6.9 | 0 |
| After 5 months at 4° C. | 0.133 | 27.0 | 65.1 | 7.9 | 0 |

*R.T. = Room Temperature

EXPERIMENTAL EXAMPLE 2

Acute Toxicity Test

The acute toxicity test on the preparations of the present invention was carried out using the preparations of the present invention shown in Table 4 which had been physiologically isotonized. The test animals used were Wister-strain male rats (weighing 100–120 g). The emulsoin was intravenously administered and the animals were observed for one week after the administration.

The results are such that with either emulsion containing perfluoro-N-cyclohexylprrolidine or perfluoro-N-(3'-methylcyclohexyl)pyrrolidine, thre was no death case at 100 ml/kg-body weight and thus their toxicity are very small.

TABLE 4

| Composition | | Ratio, % (w/v) |
|---|---|---|
| Oil Component (9 vol) | Perfluoro Compound | 30 |
| | Emulsifying Agent Vitelline Phospholipid | 4.0 |
| Electrolyte (1 vol) | NaCl | 6.00 |
| | NaHCO$_3$ | 2.1 |
| | KCl | 0.336 |
| | MgCl$_2$.6H$_2$O | 0.427 |
| | CaCl$_2$.2H$_2$O | 0.356 |
| | D-Glucose | 1.802 |
| | pH | 8.0 |

EXPERIMENTAL EXAMPLE 3

Distribution of Perfluoro-compound in Organs

Using Wister-strain male rats weighing 120–130 g, the emulsion prepared in Reference Example 1 was administered into the tail vein [at 4 g/kg as perfluoro-N-cyclohexylpyrrolidine], and for a period of 3 months after the administration, the content of said compound in the liever, spleen and fat tissues due to uptake were measured by means of gas chromatography.

The content of perfluoro-N-cyclohexylpyrrolidine uptake in each organ 1, 2 and 4 weeks and 3 months after the administration are shown in Table 5. The compound was taken up in greater amounts by the reticuloendothelial organs shortly after the administration, but soon disappeared rapidly. There was no evidence of adverse influence on the liver or spleen organ.

As a result, the half-life of perfluoro-N-hexylpyrrolidine was calculated to be 16 days.

TABLE 5

| Organ | Time after the Administration | Residual Rate of perfluoro-compound % |
|---|---|---|
| Liver | 1 Week | 21.23 |
| | 2 Weeks | 13.63 |
| | 4 Weeks | 4.98 |
| | 3 Months | 0.24 |
| Spleen | 1 Week | 12.33 |
| | 2 Weeks | 10.49 |
| | 4 Weeks | 8.52 |
| | 3 Months | 0.51 |

EXPERIMENTAL EXAMPLE 4

Anatominal Remarks

Wister-strain male rats weighing 120–130 g were administered with 4 g/kg of the perfluorocycloamine emulsion prepared in Reference Example 1 or 2, and the dissected organs were observed for a period of 3 months after the administration, and further the organs (liver and spleen) were weighed, to determine the weight relative to the body weight.

One, 2 and 4 weeks and 3 months after the administration of the emulsion, the important organs, i.e. the lung, liver and spleen were observed, to find no evidence of the influence on the organs by either said compound because of their rapid elimination.

What is claimed is:

1. An emulsion containing a perfluorocycloamine compound capable of carrying oxygen, said emulsion comprising:

5–50% (w/v) of a perfluorocycloamine compound of the formula:

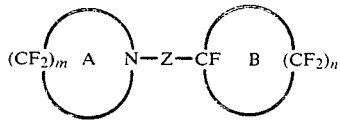

wherein
either or both of ring A and ring B may be substituted with lower perfluoroalkyl groups,
m and n are independently 4, 5 or 6, and
Z is a perfluoroalkylene group or a chemical bond, with the proviso that n is 4 or 6 when n is 4 and Z is a chemical bond,
as an oxygen carrying component;

1-5% (w/v) of an emulsifying agent, and
a physiologically acceptable aqueous solution as the balance,
the emulsion having a particle diameter of 0.3μ or less.

2. An emulsion according to claim 1 in which the perfluorocycloamine compound is present in an amount of 10 to 40% (w/v).

3. An emulsion according to claim 1 in which the particles are in the range of 0.05 to 0.3μ in diameter.

* * * * *